US010335049B2

(12) United States Patent
Griswold et al.

(10) Patent No.: US 10,335,049 B2
(45) Date of Patent: Jul. 2, 2019

(54) MAGNETIC RESONANCE FINGERPRINTING WITH STEADY STATE PRECESSION (MRF-FISP)

(71) Applicant: Case Western Reserve University, Cleveland, OH (US)

(72) Inventors: Mark Griswold, Shaker Heights, OH (US); Yun Jiang, Cleveland Heights, OH (US); Dan Ma, Cleveland, OH (US)

(73) Assignee: Case Western Reserve University, Cleveland, OH (US)

(*) Notice: Subject to any disclaimer, the term of this patent is extended or adjusted under 35 U.S.C. 154(b) by 925 days.

(21) Appl. No.: 14/682,183

(22) Filed: Apr. 9, 2015

(65) Prior Publication Data
US 2015/0301138 A1 Oct. 22, 2015

Related U.S. Application Data

(60) Provisional application No. 61/982,588, filed on Apr. 22, 2014.

(51) Int. Cl.
G01R 1/00 (2006.01)
A61B 5/026 (2006.01)
(Continued)

(52) U.S. Cl.
CPC ............ A61B 5/0263 (2013.01); A61B 5/055 (2013.01); A61B 5/4064 (2013.01);
(Continued)

(58) Field of Classification Search
CPC ....... A61B 1/00; A61B 17/00; A61B 2217/00; G01R 1/00; G06T 1/00; G06T 2200/00
See application file for complete search history.

(56) References Cited

U.S. PATENT DOCUMENTS 9,757,047 B2 9/2017 Chappell
9,851,425 B2 12/2017 Lee
2006/0244447 A1* 11/2006 Michaeli ............ G01R 33/446
324/309
2009/0142273 A1* 6/2009 Pagel .................. A61K 49/085
424/9.3
(Continued)

FOREIGN PATENT DOCUMENTS

DE 102014223388 B4 5/2016
WO WO2018065618 A1 4/2018

OTHER PUBLICATIONS

D. Ma, et al.,"Magnetic Resonance Fingerprinting", Nature, Mar. 14, 2013, 187-192, 495-7440, Macmillan Publishers Limited, United States.
(Continued)

Primary Examiner — Jermele M Hollington
Assistant Examiner — Temilade S Rhodes-Vivour
(74) Attorney, Agent, or Firm — Quarles & Brady LLP

(57) ABSTRACT

Example embodiments associated with NMR fingerprinting are described. One example NMR apparatus includes an NMR logic that repetitively and variably samples a (k, t, E) space associated with an object to acquire a set of NMR signals that are associated with different points in the (k, t, E) space. Sampling is performed with t and/or E varying in a non-constant way. Sampling is performed in response to a fast imaging with steady state free precession (MRF-FISP) pulse sequence having an unbalanced gradient that dephases transverse magnetization. The NMR apparatus may also include a signal logic that produces an NMR signal evolution from the NMR signals, and a characterization logic that characterizes a resonant species in the object as a result of comparing acquired signals to reference signals. The unbalanced gradient in the MRF-FISP pulse sequence reduces sensitivity to B0 in homogeneity.

26 Claims, 19 Drawing Sheets

(51) Int. Cl.

| | | |
|---|---|---|
| *A61B 5/055* | (2006.01) | |
| *G01R 33/44* | (2006.01) | |
| *G01R 33/48* | (2006.01) | |
| *G01R 33/565* | (2006.01) | |
| *G01R 33/56* | (2006.01) | |
| *G01R 33/561* | (2006.01) | |
| *A61B 5/00* | (2006.01) | |
| *G01R 33/563* | (2006.01) | |
| *A61B 1/00* | (2006.01) | |
| *A61B 17/00* | (2006.01) | |
| *G06T 1/00* | (2006.01) | |
| *G01R 33/50* | (2006.01) | |

(52) U.S. Cl.
CPC ....... *G01R 33/448* (2013.01); *G01R 33/4818* (2013.01); *G01R 33/5602* (2013.01); *G01R 33/5608* (2013.01); *G01R 33/5611* (2013.01); *G01R 33/56366* (2013.01); *G01R 33/56563* (2013.01); *A61B 1/00* (2013.01); *A61B 5/742* (2013.01); *A61B 17/00* (2013.01); *A61B 2217/00* (2013.01); *A61B 2218/00* (2013.01); *G01R 1/00* (2013.01); *G01R 33/4828* (2013.01); *G01R 33/50* (2013.01); *G06T 1/00* (2013.01); *G06T 2200/00* (2013.01)

(56) References Cited

U.S. PATENT DOCUMENTS

| | | | |
|---|---|---|---|
| 2011/0199084 A1* | 8/2011 | Hasan | A61B 5/055 324/309 |
| 2012/0262165 A1* | 10/2012 | Griswold | G01R 33/50 324/309 |
| 2012/0262166 A1* | 10/2012 | Griswold | G01R 33/50 324/309 |
| 2013/0271132 A1* | 10/2013 | Griswold | G01R 33/5612 324/309 |
| 2014/0084922 A1 | 3/2014 | Fu | |
| 2014/0167754 A1 | 6/2014 | Jerecie | |
| 2014/0292330 A1* | 10/2014 | Gulani | G01R 33/3614 324/309 |
| 2016/0282430 A1 | 9/2016 | Gulani | |
| 2017/0146623 A1 | 5/2017 | Cohen | |

OTHER PUBLICATIONS

B.A. Garner, Modern Legal Use, A Dictionary of Modern Legal Usage, 1995, 624, 2, Oxford University Press Inc., Oxford.
O. Heid et al., Quest—a quick echo split NMR Imaging Technique, Magnetic Resonance in Medicine, Feb. 1993, 280-283, 29-2, Wiley-Liss, Inc., United States.

* cited by examiner

MAGNETIC RESONANCE FINGERPRINTING WITH STEADY STATE PRECESSION (MRF-FISP)

CROSS REFERENCE TO RELATED APPLICATIONS

This application claims priority to U.S. Provisional Patent Application 61/982,588 filed Apr. 22, 2014.

FEDERAL FUNDING NOTICE

The invention was made with government support under the grant(s) HL094557 and EB017219 awarded by the National Institutes of Health. The government has certain rights in the invention.

BACKGROUND

Characterizing resonant species using nuclear magnetic resonance (NMR) can include identifying different properties of a resonant species (e.g., T1 spin-lattice relaxation, T2 spin-spin relaxation, proton density). Other properties like tissue types, and super-position of attributes can also be identified using NMR signals. These properties and others may be identified simultaneously using magnetic resonance fingerprinting (MRF), which is described in *Magnetic Resonance Fingerprinting*, Ma D et al., Nature 2013:495, (7440): 187-192.

Conventional magnetic resonance (MR) pulse sequences include repetitive similar preparation phases, waiting phases, and acquisition phases that serially produce signals from which images can be made. The preparation phase determines when a signal can be acquired and determines the properties of the acquired signal. For example, a first pulse sequence may produce a T1-weighted signal at a first echo time (TE) while a second pulse sequence may produce a T2-weighted signal at a second TE. These conventional pulse sequences typically provide qualitative results where data are acquired with various weightings or contrasts that highlight a particular parameter (e.g., T1 relaxation, T2 relaxation).

When MR images are generated, they may be viewed by a radiologist and/or surgeon who interprets the qualitative images for specific disease signatures. The radiologist may examine multiple image types (e.g., T1-weighted, T2-weighted) acquired in multiple imaging planes to make a diagnosis. The radiologist or other individual examining the qualitative images may need particular skill to be able to assess changes from session to session, from machine to machine, and from machine configuration to machine configuration. Additionally, the reviewer or interpreter may need to make their assessment in light of artifacts or other suboptimal image components caused by, for example, inhomogeneity in the main magnetic field B0.

Unlike conventional MRI, MRF employs a series of varied sequence blocks that simultaneously produce different signal evolutions in different resonant species (e.g., tissues) to which the RF is applied. The term "resonant species", as used herein, refers to an item (e.g., water, fat, tissue, material) that can be made to resonate using NMR. By way of illustration, when RF energy is applied to a volume that has bone and muscle tissue, then both the bone and muscle tissue will produce an NMR signal. However the "bone signal" and the "muscle signal" will be different and can be distinguished using MRF. The different signals can be collected over a period of time to identify a signal evolution for the volume. Resonant species in the volume can then be characterized by comparing the signal evolution to known evolutions. Characterizing the resonant species may include identifying a material or tissue type, or may include identifying MR parameters associated with the resonant species. The "known" evolutions may be, for example, simulated evolutions or previously acquired evolutions. A large set of known evolutions may be stored in a dictionary. The ability to match evolutions may, in some instances, be somewhat compromised by varying conditions in an MR environment including, for example, an inhomogeneity in the main magnetic field B0.

Different pulse sequences have been employed with MRF. For example, both balanced steady state free precession (bSSFP) and Quick Echo Split Technique (QUEST) have been employed with MRF. QUEST is described in Heid O, Deimling M, and Huk W. QUEST—A Quick Echo Split NMR Imaging Technique, *Magn Reson Med* 1993; 29:280-283. MRF with both bSSFP and QUEST have demonstrated the efficiency of MRF in estimating multiple relaxation parameters simultaneously. Unfortunately, some MRF pulse sequences may have had some susceptibility to an inhomogeneity in the main magnetic field B0.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Example apparatus and methods simultaneously acquire quantitative data concerning magnetic resonance (MR) parameters for resonant species in an object using magnetic resonance fingerprinting (MRF) that uses a steady state precession (FISP) pulse sequence (MRF-FISP). Example MRF-FISP apparatus and methods perform rapid quantification of multiple relaxation parameters in a manner that is less sensitive to inhomogeneity in the main magnetic field B0. The MRF-FISP pulse sequence is less sensitive to the inhomogeneity, at least in part, because the MRF-FISP sequence has unbalanced gradient moments in between RF pulses. The unbalanced gradient moments make the sequence more immune to B0 inhomogeneity due, at least in part, to controlling transverse magnetization dephasing. The increased immunity to B0 inhomogeneity improves over conventional systems by increasing the ability to add sensitivity to additional parameters including diffusion and perfusion.

Figure 1:
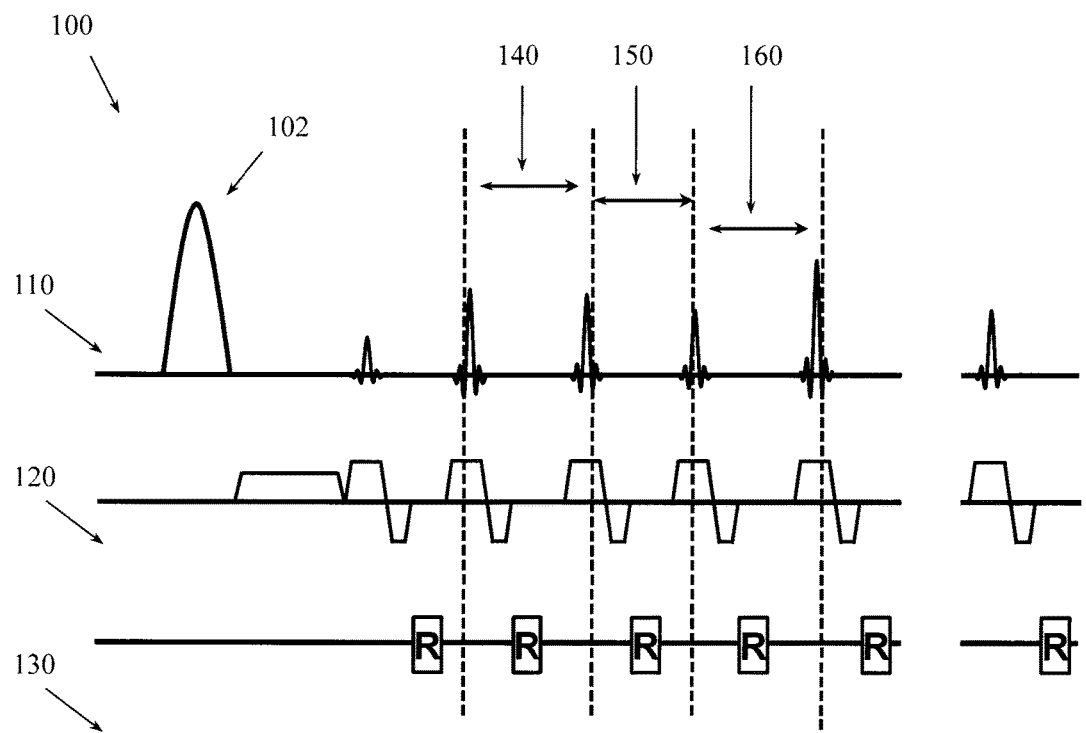
FIG. 1 illustrates an example magnetic resonance fingerprinting with steady state free precession (MRF-FISP) pulse sequence with unbalanced gradients.
Figure 19:
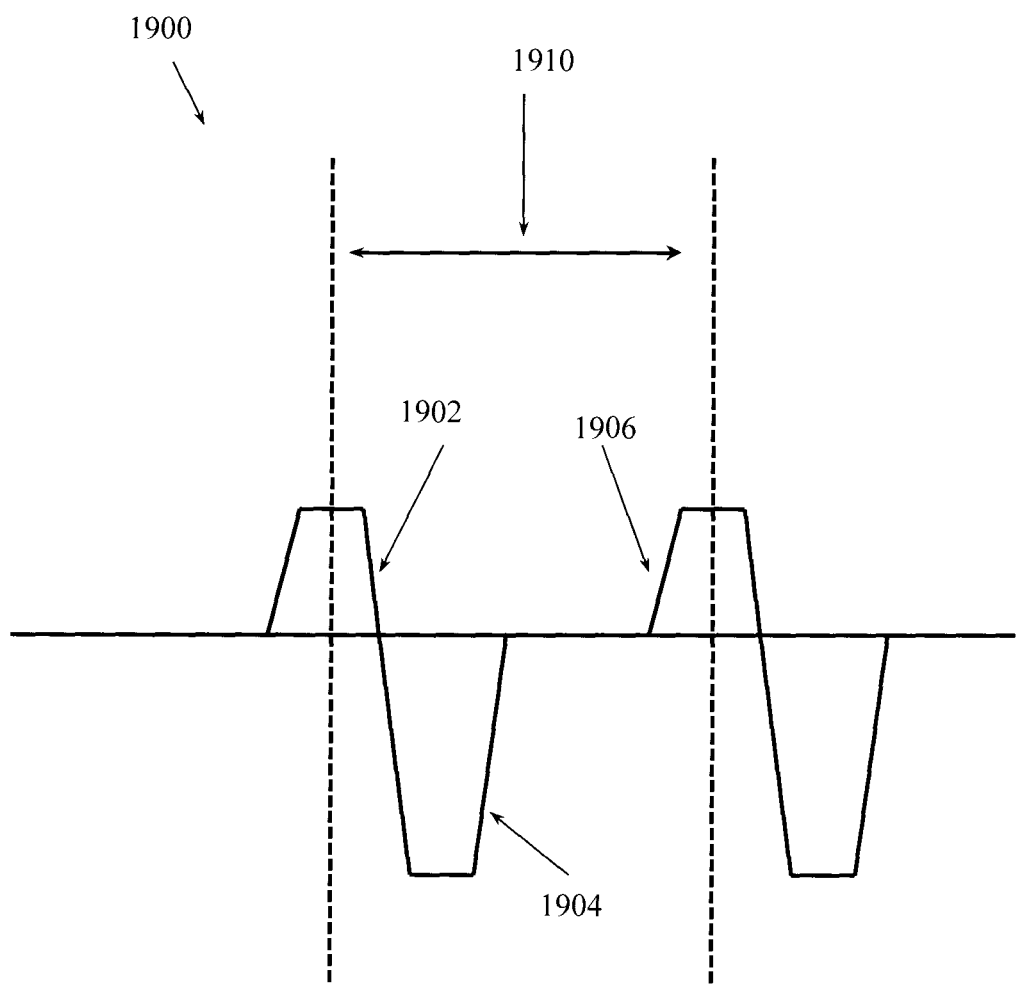
FIG. 19 illustrates a portion of an example MRF-FISP pulse sequence.

FIG. 1 illustrates an example MRF-FISP pulse sequence 100. The MRF-FISP pulse sequence 100 includes a radio frequency (RF) inversion pulse 102 in the RF energy 110 applied. While an inversion pulse 102 is illustrated, in different embodiments there may or may not be an inversion recovery period. The MRF-FISP pulse sequence 100 includes an unbalanced slice select gradient 120. While slice select gradient 120 is illustrated as being unbalanced, in different embodiments other gradients (e.g., x, y, z, phase encoding, frequency encoding, readout encoding) may be unbalanced. The unbalanced slice select gradient 120 dephases transverse magnetization produced during MRF of the object. In one embodiment, other than T2 or T2* decay, only the unbalanced slice select gradient 120 dephases the transverse magnetization. Controlling the dephasing of transverse magnetization in this manner improves immunity to artifacts or other distortions caused by an imperfect B0. In the MRF-FISP pulse sequence 100, the acquisition periods 140, 150, and 160 do not have to be of equal duration. However, in one preferred embodiment, the acquisition periods 140, 150, and 160 will be equal. FIG. 19 illustrates a portion of an MRF-FISP pulse sequence 1900. One acquisition period 1910 is illustrated. The area 1902 usually cancels the area 1904 leaving the area 1906 as residual.

The MRF-FISP algorithm can be manipulated to generate different contrasts by varying flip angles or acquisition periods used in the MRF-FISP pulse sequence 100. Thus, in one embodiment, to generate unique signal shapes for different tissue types that may be examined using MRF-FISP, example apparatus and methods may vary flip angle or acquisition time in different acquisition periods. In one embodiment, a flip angle or repetition time may be varied from one acquisition period to the next.

Figure 2:
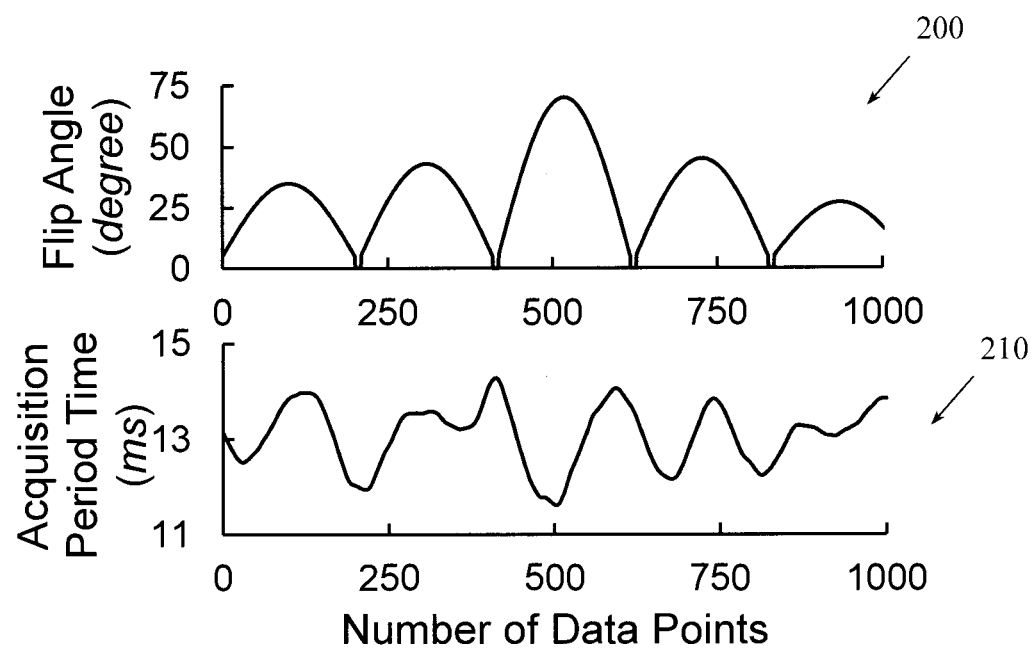
FIG. 2 illustrates a sinusoidal variation of flip angles and repetition times or acquisition periods (TRs) associated with an example MRF-FISP pulse sequence.

FIG. 2 illustrates one example manipulation of flip angle 200 and acquisition time 210 in an example MRF-FISP pulse sequence. In one embodiment, a sinusoidal variation of flip angles and acquisition times per acquisition period may be employed in a Perlin noise pattern.

The unbalanced gradient 120 illustrated in pulse sequence 100 (FIG. 1), combined with the variations in flip angle 200 and acquisition period 210 illustrated in FIG. 2 produced $2\pi$ dephasing within one voxel. Achieving $2\pi$ dephasing or more within one voxel makes data acquired using the MRF-FISP sequence insensitive to B0 inhomogeneity. While $2\pi$ dephasing is described, other dephasing (e.g., $8\pi$) may be employed.

Figure 3:
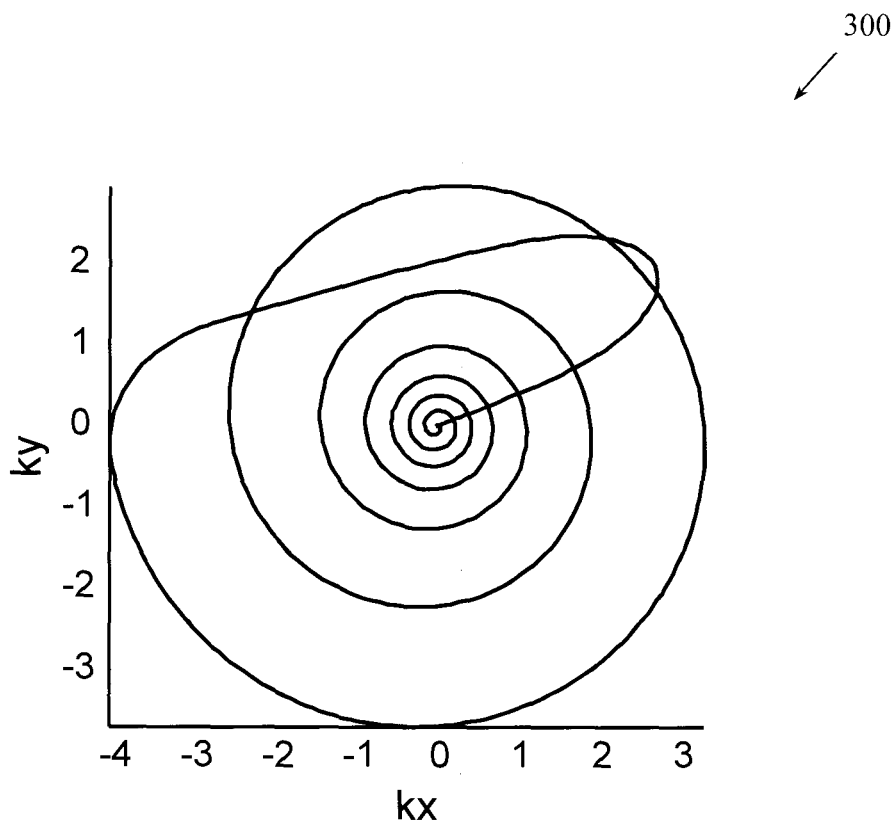
FIG. 3 illustrates an example variable density spiral trajectory used to read out data produced using an example MRF-FISP sequence.

Example apparatus and methods may acquire data in response to the MRF-FISP pulse sequence using different acquisition strategies. In one embodiment, a variable-density spiral trajectory using minimum-time gradient design may be used to acquire data in response to the MRF-FISP pulse sequence. FIG. 3 illustrates one example variable-density spiral trajectory 300. The trajectory 300 may be used to read out the data using readout 130 (FIG. 1).

One example variable density spiral trajectory may use a small number of interleaves to fully sample an inner region of k-space. An "inner region of k-space" refers to, for example, a central region of k-space data associated with a slice being acquired. The central region may be centered on or positioned with respect to, for example, the center of k-space. In one example, six interleaves may be used to sample a 20×20 region centered in the center of k-space. In other examples, different numbers of interleaves may be used to sample different inner region sizes. Similarly, a larger number of interleaves may be used to fully sample an outer region of k-space. An "outer region of k-space" refers to, for example, a region outside the inner region or outside the center region of k-space. In one embodiment, forty-eight interleaves may be used to fully sample an outer 256×256 region. In one embodiment, a spiral interleaf may be used in each separate acquisition period. The trajectory may be rotated by an amount (e.g., 7.5 degrees) per acquisition period.

Example apparatus and methods may reconstruct the data acquired using the variable density spiral trajectory in different ways. In one example, the data may be reconstructed using a non-uniform fast Fourier transform (NUFFT). In other examples, the data may be reconstructed using approaches including, but not limited to, non-equi-spaced FFTs (NFFT) or unequally-spaced FFTs (USFFT).

MRF simultaneously provides quantitative data concerning multiple MR parameters. Observed signal evolutions are matched to dictionary entries using, for example, template matching or other matching or comparing processes. In one example matching process, the inner product is computed between a noisy acquired signal and entries in a dictionary to find the stored signal evolution to which an acquired signal evolution most closely matches. In other examples, other pattern matching or similarity finding approaches are performed. Values for MR parameters related to the dictionary entry that matched the acquired noisy signal may then be retrieved. In one example, MR parameters may be stored in the dictionary, while in another example MR parameters may be stored in a data store separate from the dictionary. Example apparatus and methods match dictionary entries to signals acquired in response to an MRF-FISP pulse sequence using a variable density spiral readout.

In one embodiment, a dictionary containing the signal evolutions with a range of T1 (10~5000 ms) and T2 (5~500 ms) was created using an extended phase graph (EPG) algorithm with different acquisition parameters. Dictionaries containing signal evolutions with different T1 and T2 ranges may be created using different approaches including, for example, the Bloch simulation approach. The EPG approach may simulate the expected signal more quickly than the Bloch approach because the EPG approach may not have to consider multiple spins as in the Bloch approach.

Figure 4:
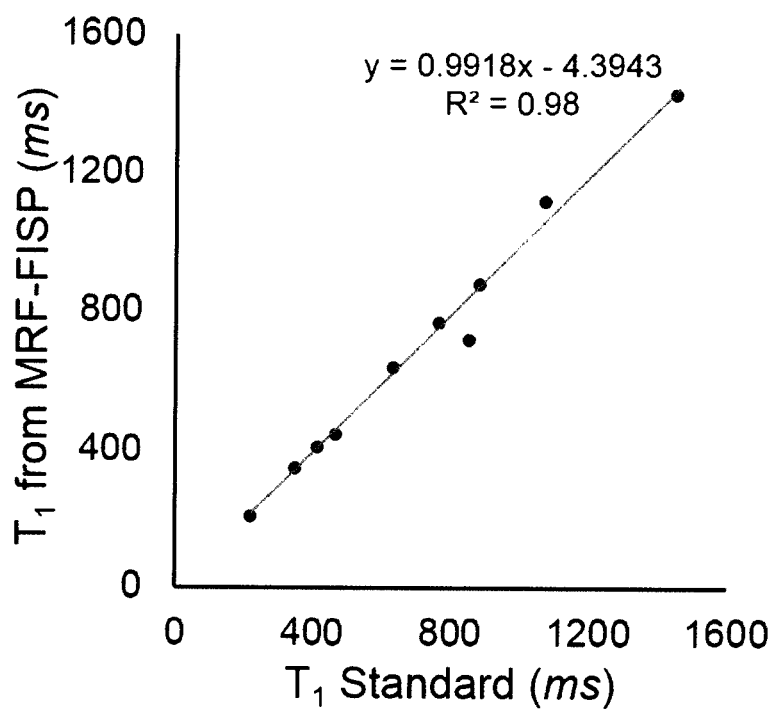
FIG. 4 compares T1 values produced using an example MRF-FISP approach and a conventional spin-echo method.

FIG. 4 illustrates T1 values produced using an example MRF-FISP approach and a conventional spin-echo method. There is good agreement between the measurements (e.g., y=0.9918x−4.3943, $R^2$=0.98).

Figure 5:
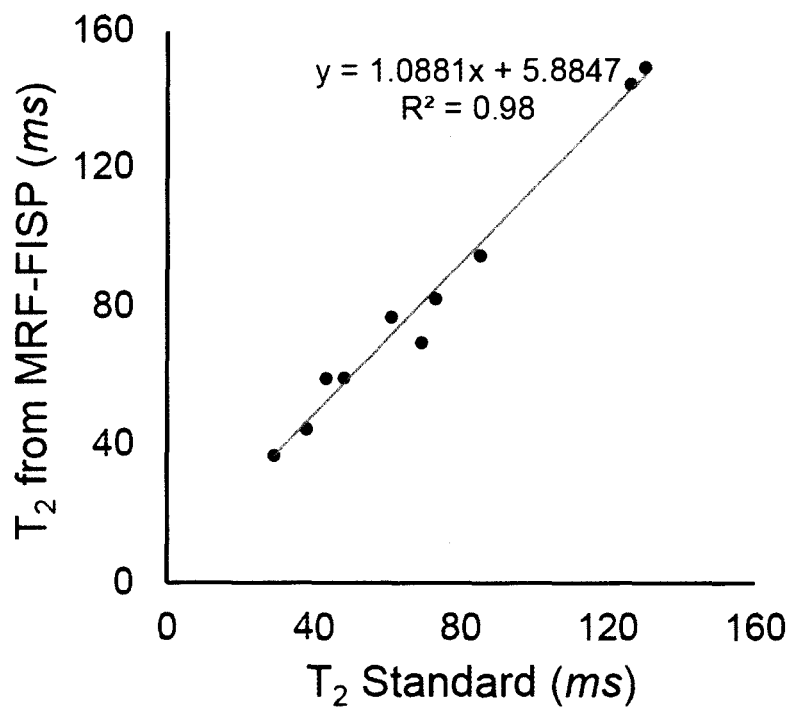
FIG. 5 compares T2 values produced using an example MRF-FISP approach and a conventional spin-echo method.

FIG. 5 illustrates T2 values produced using an example MRF-FISP approach and a conventional spin-echo method. There is good agreement between the measurements (e.g., y=1.0881x+5.8847, $R^2$=0.98).

Figure 6:
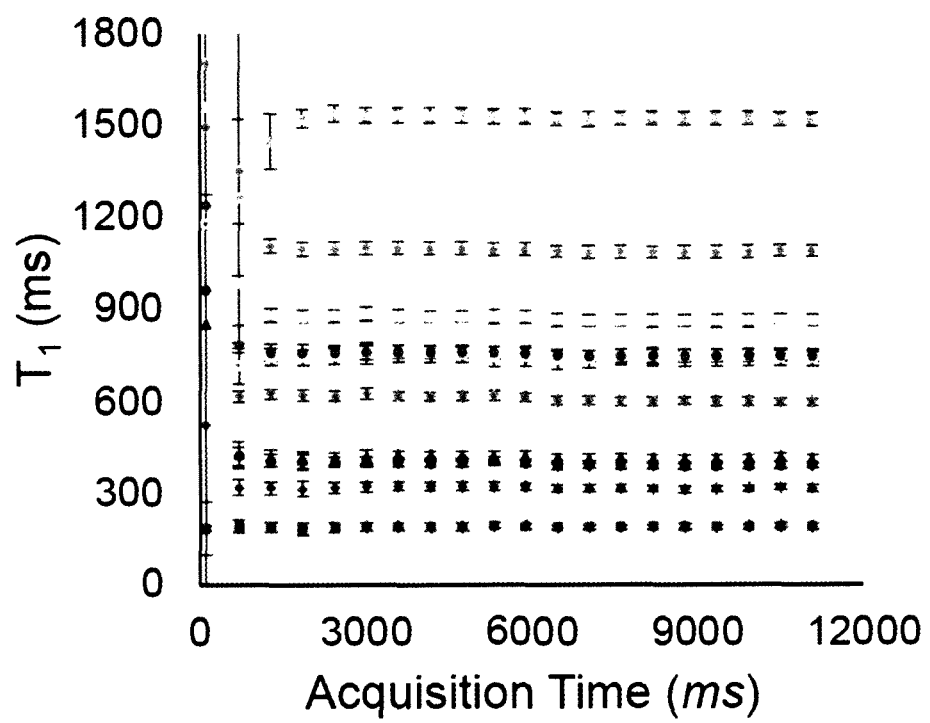
FIG. 6 compares T1 values and standard deviations measured by example MRF-FISP with different acquisition times.
Figure 7:
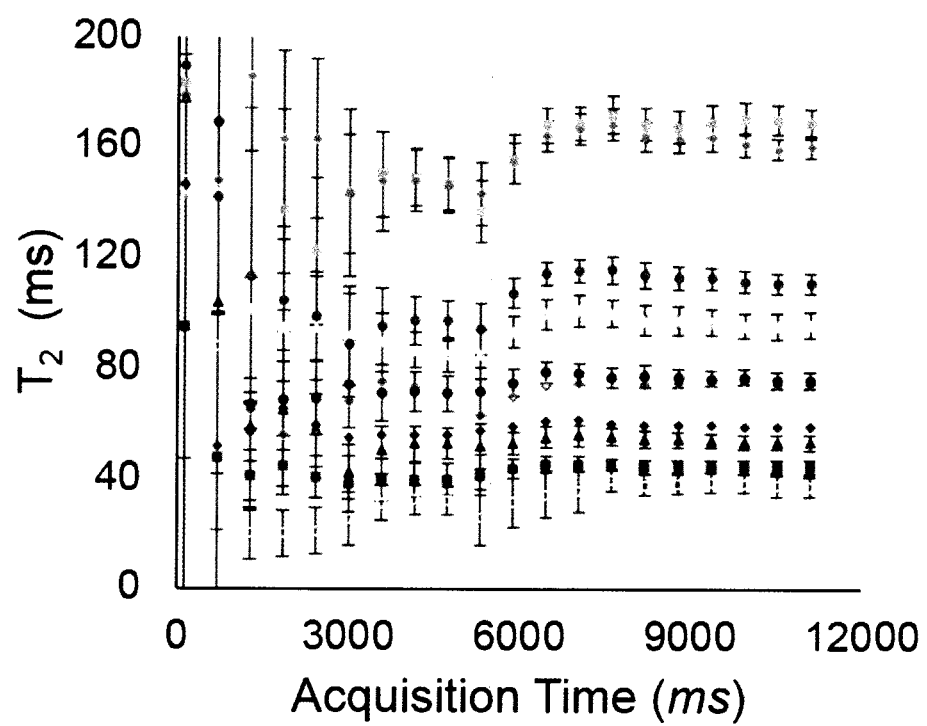
FIG. 7 illustrates T2 values and standard deviations measured by example MRF-FISP with different acquisition times.

FIG. 6 illustrates T1 values and standard deviations measured by MRF-FISP with different acquisition times. FIG. 7 illustrates T2 values and standard deviations measured by MRF-FISP with different acquisition times. FIGS. 6 and 7 both demonstrate that MRF-FISP produces smaller errors as new information is added over time during the MRF-FISP acquisition. The results illustrated in FIGS. 4-7 demonstrate that MRF-FISP is in good agreement with the conventional measurements.

Figure 8:
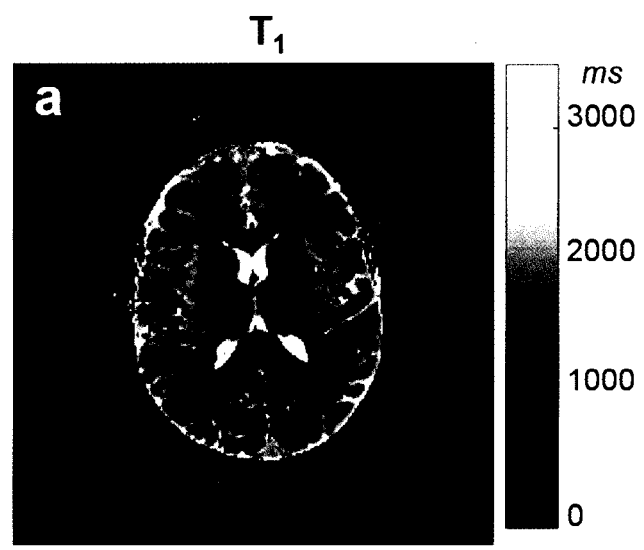
FIG. 8 illustrates a T1 map for an asymptomatic volunteer produced using an example MRF-FISP approach.
Figure 9:
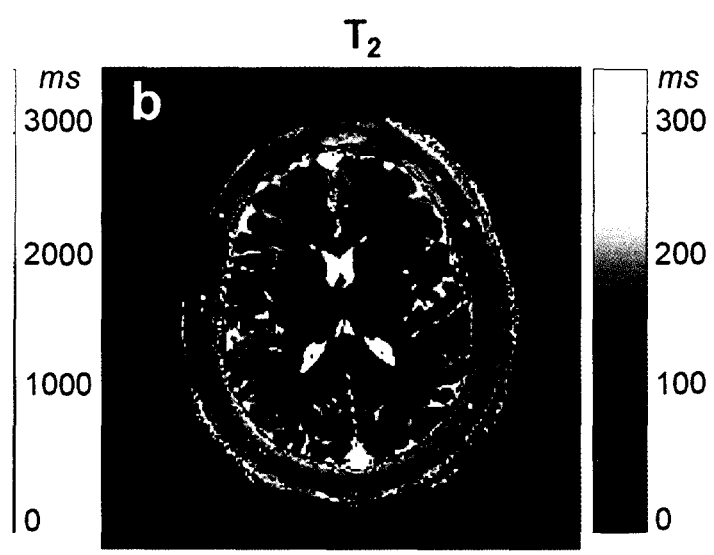
FIG. 9 illustrates a T2 map for an asymptomatic volunteer produced using an example MRF-FISP approach.
Figure 10:
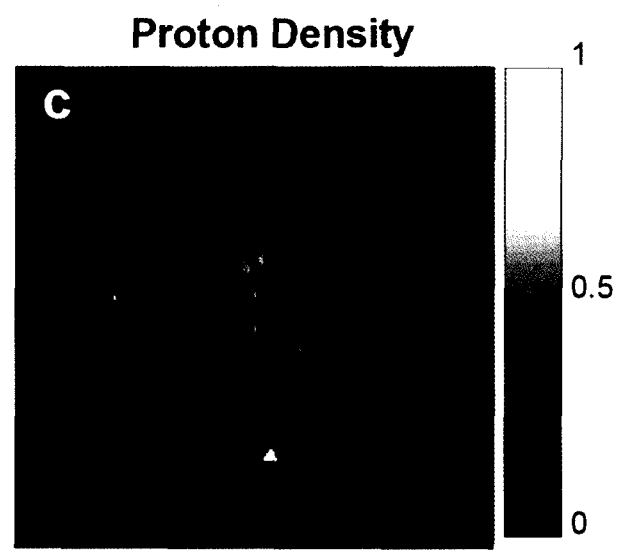
FIG. 10 illustrates a proton density map for an asymptomatic volunteer produced using an example MRF-FISP approach.

FIGS. 8-13 illustrate actual images produced by an example MRF-FISP approach. FIG. 8 illustrates a T1 map for an asymptomatic volunteer. The T1 map was produced using an example MRF-FISP approach. FIG. 9 illustrates a T2 map for the volunteer. The T2 map was produced using an example MRF-FISP approach. FIG. 10 illustrates a proton density map for the volunteer. The proton density map was produced using an example MRF-FISP approach.

Figure 11:
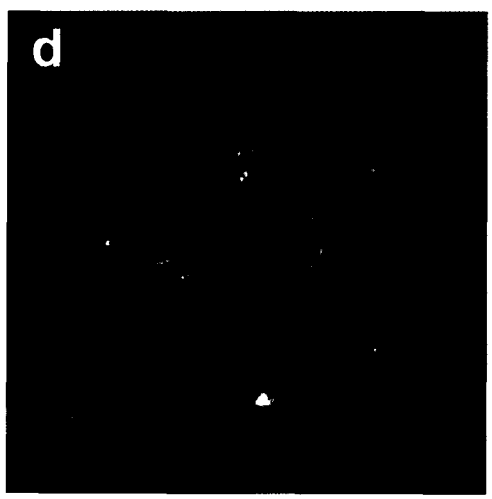
FIG. 11 illustrates a proton density weighted map for an asymptomatic volunteer produced using an example MRF-FISP approach.
Figure 12:
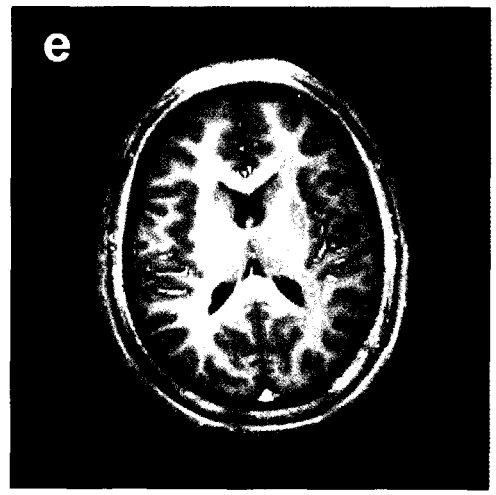
FIG. 12 illustrates a T1 weighted map for an asymptomatic volunteer produced using an example MRF-FISP approach.
Figure 13:
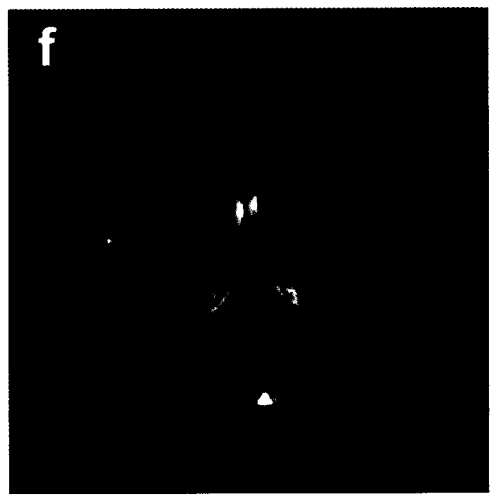
FIG. 13 illustrates a T2 weighted map for an asymptomatic volunteer produced using an example MRF-FISP approach.

FIG. 11 illustrates a proton density weighted map for the volunteer. The proton density weighted map was produced using an example MRF-FISP approach. FIG. 12 illustrates a T1 weighted map for the volunteer. The T1 weighted map was produced using an example MRF-FISP approach. FIG. 13 illustrates a T2 weighted map for the volunteer. The T2 weighted map was produced using an example MRF-FISP approach. Mean values computed for T1 and T2 from both white matter and gray matter were in good agreement with published results.

The results illustrated in FIGS. 4-13 demonstrate that an MRF-FISP pulse sequence having an unbalanced gradient can produce accurate quantification of relaxation parameters including T1, T2, and proton density. Using the unbalanced gradient makes the MRF-FISP sequence less sensitive to B0 inhomogeneity. Being less sensitive to B0 inhomogeneity facilitates extending MRF for applications in organs (e.g., heart) where obtaining a homogenous B0 field may be a challenge. Being less sensitive to B0 inhomogeneity also facilitates extending MRF to higher field apparatus (e.g., 7T) where obtaining a homogenous B0 field may also be a challenge. Being less sensitive to B0 inhomogeneity also facilitates extending MRF into quantifying additional MR parameters including but not limited to diffusion and perfusion.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage medium", as used herein, refers to a non-transitory medium that stores signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, an ASIC, a CD, other optical medium, a RAM, a ROM, a memory chip or card, a memory stick, and other media from which a computer, a processor or other electronic device can read.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"User", as used herein, includes but is not limited to one or more persons, software, computers or other devices, or combinations of these.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 14:
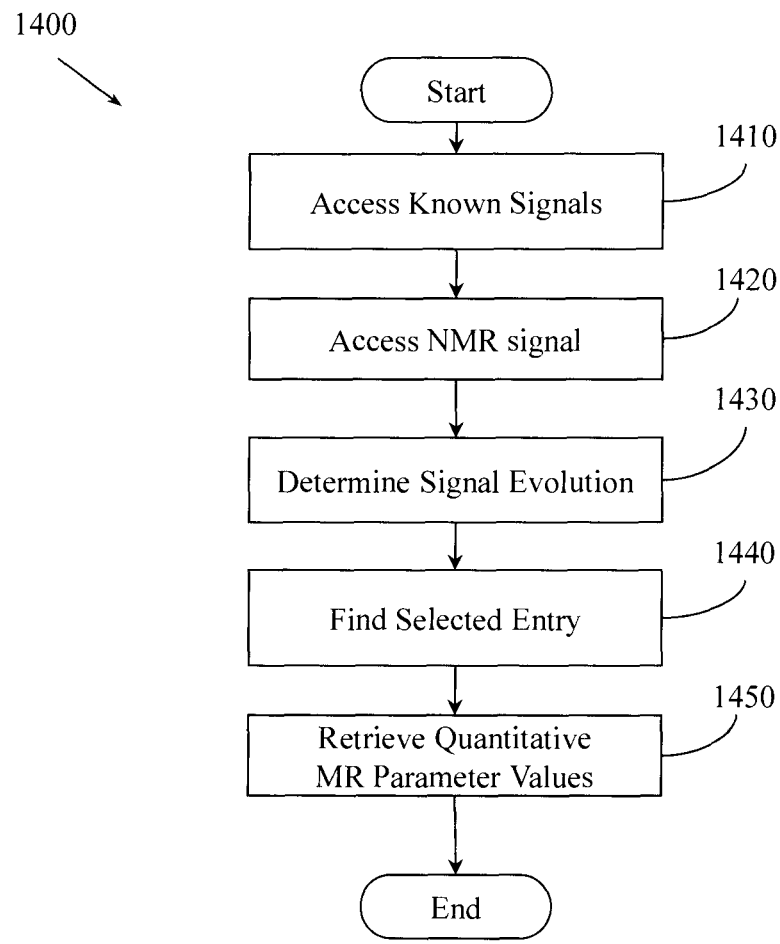
FIG. 14 illustrates an example method associated with MRF-FISP.

FIG. 14 illustrates a method 1400 associated with MRF-FISP. Method 1400 includes, at 1410, accessing a set of known signal evolutions. In one embodiment, the set of known signal evolutions were created using an extended phase graph approach.

Method 1400 also includes, at 1420, accessing an acquired NMR signal. The acquired NMR signal is produced by a volume that contains one or more resonant species that simultaneously produced individual NMR signals in response to MRF excitation that employed an MRF-FISP pulse sequence.

In one embodiment, the MRF-FISP pulse sequence has an unbalanced gradient that dephases transverse magnetization produced in the volume. The unbalanced gradient may dephase transverse magnetization by at least $2\pi$ within one voxel. The acquired NMR signal is insensitive to B0 inhomogeneity due, at least in part, to the unbalanced gradient that dephases the transverse magnetization. While $2\pi$ dephasing is described, other dephasing (e.g., $8\pi$) may be employed.

In one embodiment, accessing the NMR signal at 1420 may include controlling the MRF-FISP pulse sequence to employ a variable density spiral readout trajectory. In one embodiment, the MRF-FISP pulse sequence may have a variable density spiral readout having a minimum-time gradient design. In one embodiment, the variable density spiral readout trajectory may use M interleaves to fully sample an inner region of k space, M being an integer. The variable density spiral readout trajectory may also use N interleaves to fully sample an outer region of k space. In one embodiment, N is an integer greater than M. Different values of M and N may be employed. In one embodiment, the variable density spiral readout trajectory uses one spiral interleaf per acquisition period. In one embodiment, the variable density spiral readout trajectory may rotate per acquisition period.

Method 1400 also includes, at 1430, controlling the NMR apparatus to determine a signal evolution from the acquired NMR signals. Determining the signal evolution may include storing (k, t, E) space data points acquired during action 1420. While an individual sequence block may yield a single point in (k, t, E) space, the signal evolution is determined by the series of variable sequence blocks. In one embodiment, the simultaneously produced signals are acquired at 1420 over a first period of time and the signal evolution is determined at 1430 over a second period of time.

Method 1400 also includes, at 1440, finding a selected entry in the set of known signal evolutions that matches the signal evolution. Finding the selected entry may include comparing first information (e.g., observed signal evolution) to reference information (e.g., MRF dictionary entries) to find a selected entry in the reference information. Comparing the first information may include pattern matching or other processes that determine how similar the first information is to the reference information. The reference information may include signal evolutions associated with healthy tissue, normal tissue, abnormal tissue, diseased tissue, vasculature, tumors, lesions, or other pathology. The first information may be, for example, the signal evolution. The reference information may be, for example, known, stored, simulated, and/or predicted signal evolutions. The reference information may also include information that is produced as a function of a known, stored, simulated, or predicted signal evolution. The reference information may be produced by, for example, transforming a signal evolution, combining signal evolutions, decomposing signal evolutions, and other operations. In different examples, the "stored" signal evolutions may include previously acquired signals, simulated signals, or both. In one embodiment, the stored signal evolutions are associated with signals not acquired from the object while in another embodiment the stored signal evolutions are associated with signals acquired from the object. In one embodiment, the stored signals may be associated with signals acquired from the object being analyzed and signals not acquired from the object being analyzed.

The stored signals and information derived from reference signal evolutions may be associated with a potentially very large data space. The data space for signal evolutions can be partially described by:

$$SE = \sum_{i=1}^{N_S} \prod_{i=1}^{N_A} \sum_{j=1}^{N_{RF}} R_{i(\alpha)} R_{RF_{ij}(\alpha,\Phi)} R(G) E_i(T1, T2, \ldots) DPdM_0$$

where:
SE is a signal evolution,
$N_S$ is a number of spins,
$N_A$ is a number of sequence blocks,
$N_{RF}$ is a number of RF pulses in a sequence block,
$\alpha$ is a flip angle,
$\Phi$ is a phase angle,
$R_i(\alpha)$ is a rotation due to off resonance,
$R_{RF_{ij}}(\alpha,\Phi)$ is a rotation due to RF differences,
$R(G)$ is a rotation due to a gradient,
T1 is spin-lattice relaxation,
T2 is spin-spin relaxation,
D is diffusion relaxation,
Pd is proton density, $E_i(T1, T2, \ldots)$ is associated with magnetization changes, and $M_0$ is the default or equilibrium magnetization.

Additionally or alternatively, the summation on j could be replaced by a product on j, e.g.:

$$SE = \sum_{i=1}^{N_S} \prod_{i=1}^{N_A} \prod_{j=1}^{N_{RF}} R_{i(\alpha)} R_{RF_{ij}(\alpha,\Phi)} R(G) E_i(T1, T2, \ldots) DPdM_0$$

In one embodiment, the dictionary may store signals described by:

$$S_i = R_i E_i (S_{i-1})$$

where:

$S_0$ is the default or equilibrium magnetization, $S_i$ is a vector that represents the different components of magnetization Mx, My, Mz during acquisition block i, $R_i$ is a combination of rotational effects that occur during acquisition block i, and $E_i$ is a combination of effects that alter the amount of magnetization in the different states for acquisition block i. In this embodiment, the signal at acquisition block i is a function of the previous signal at acquisition block i−1. Additionally or alternatively, the dictionary may store signals described by:

$$S_i = R_i E_i \sum_{x=1}^{i-1} R_x E_x (S_x)$$

or $$S_i = R_i E_i \prod_{x=1}^{i-1} R_x E_x (S_x).$$

In this embodiment, the signal is a function of the current relaxation and rotation effects and of previous acquisitions. Additionally or alternatively, the dictionary may store signals described by:

$$S_i = \sum_{s=1}^{N_s} R_{s,i} E_{s,i} (S_{s,i-1}).$$

In this embodiment, voxels have multiple resonant species or spins, and the effects may be different for every spin within a voxel. Additionally or alternatively, the dictionary may store signals described by:

$$S_i = \sum_{s=1}^{N_s} R_{s,i} E_{s,i} \sum_{x=1}^{i-1} R_{s,x} E_{s,x} (S_{s,x})$$

or $$S_i = \sum_{s=1}^{N_s} R_{s,i} E_{s,i} \prod_{x=1}^{i-1} R_{s,x} E_{s,x} (S_{s,x})$$

In this embodiment, voxels may have multiple resonant species or spins, and the effects may be different for spins within a voxel, and thus the signal may be a function of the effects and the previous acquisition blocks.

Method 1400 also includes, at 1450, retrieving quantitative MR parameter values associated with the resonant species. Retrieving quantitative MR parameter values may include retrieving, from stored MR parameters associated with the selected entry, quantitative values for T1 relaxation associated with the resonant species, T2 relaxation associated with the resonant species, or proton density associated with the resonant species. In one embodiment, method 1400 may improve over conventional systems by identifying additional MR parameters that are available due to the increased immunity to B0 inhomogeneity. The additional MR parameters may include quantitative values for diffusion, or perfusion.

Method 1400 may also produce quantitative maps from the quantitative values. The quantitative maps may describe, for example, T1 relaxation associated with the resonant species, T2 relaxation associated with the resonant species, proton density, diffusion, perfusion, or other attributes. In one embodiment the quantitative maps may be produced simultaneously (e.g., in parallel).

While FIG. 14 illustrates various actions occurring in serial, it is to be appreciated that various actions illustrated in FIG. 14 could occur substantially in parallel. By way of illustration, a first process could control accessing known signals, a second process could control acquiring NMR signals and determining a signal evolution, a third process could perform comparisons, and a fourth process could retrieve quantitative MR parameter values. While four processes are described, it is to be appreciated that a greater and/or lesser number of processes could be employed.

Figure 15:
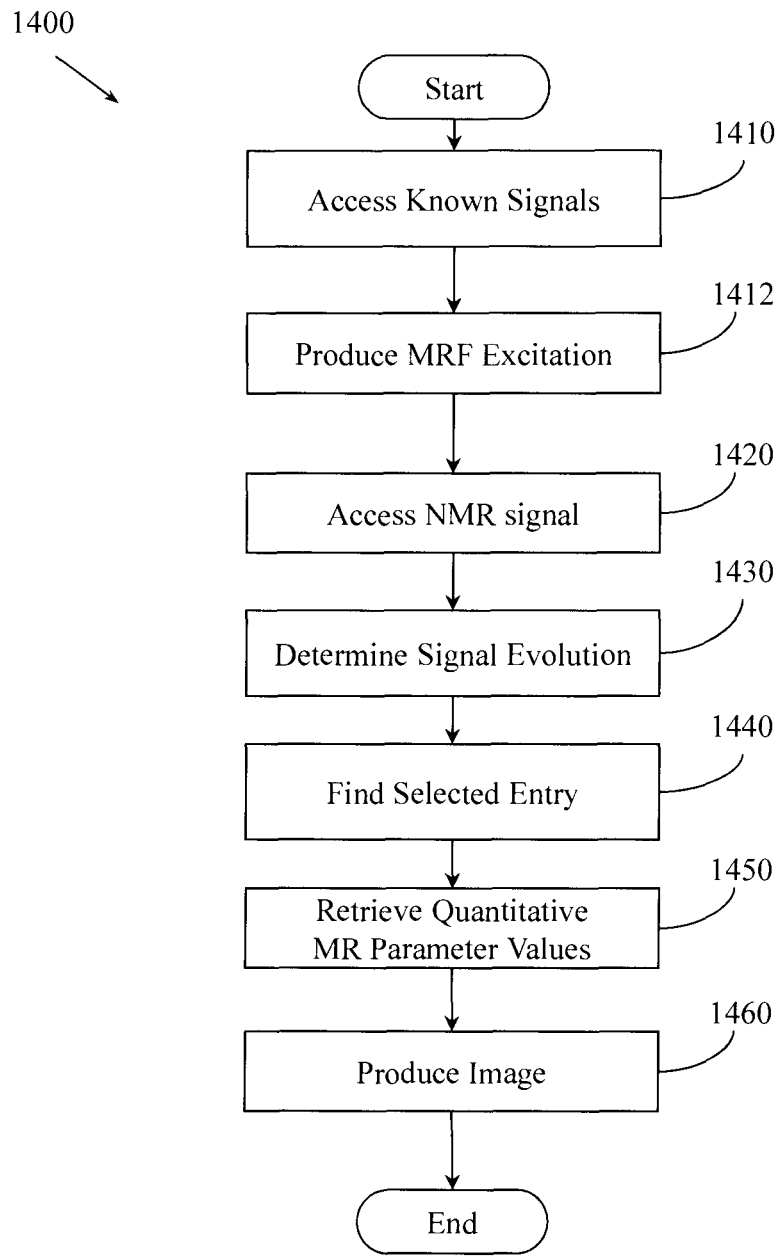
FIG. 15 illustrates an example method associated with MRF-FISP.

FIG. 15 illustrates another embodiment of method 1400 (FIG. 14). This embodiment includes actions 1410, 1420, 1430, 1440, and 1450. However, this embodiment also includes actions 1412 and 1460. Action 1412 includes controlling the MRF apparatus to produce the MRF excitation using the MRF-FISP pulse sequence. Producing the MRF excitation is performed by applying RF energy to the volume in the object in a series of variable sequence blocks. Recall that an MRF sequence block includes one or more excitation phases, one or more readout phases, and one or more waiting phases. Recall also that at least one member of the series of variable sequence blocks differs from at least one other member of the series of variable sequence blocks in one or more sequence block parameters. The MRF-FISP pulse sequence has an unbalanced gradient that dephases transverse magnetization produced in the volume.

In one embodiment, action 1412 includes controlling the NMR apparatus to vary a flip angle associated with the MRF-FISP pulse sequence or to vary the acquisition period in the MRF-FISP pulse sequence. Action 1412 may also include varying other sequence block parameters including, but not limited to, echo time, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, an amount by which a gradient is unbalanced when applied between an excitation portion of a sequence block and a readout portion of a sequence bock, a type of gradient applied between a readout portion of a sequence block and an excitation portion of a sequence block, a number of gradients applied between a readout portion of a sequence block and an excitation portion of a sequence block, an amount by which a gradient is unbalanced when applied between a readout portion of a sequence block and an excitation portion of a sequence bock, a type of gradient applied during a readout portion of a sequence block, number of gradients applied during a readout portion of a sequence block, amount of RF spoiling, or an amount of gradient spoiling.

Action 1412 may also include controlling the MRF apparatus to vary the amount of time between sequence blocks in the series of variable sequence blocks, the relative amplitude of RF pulses in sequence blocks in the series of variable sequence blocks, or the relative phase of RF pulses in sequence blocks in the series of variable sequence blocks.

This embodiment of method 1400 also includes, at 1460, producing an image. The image may be a T1 weighted image, a T2 weighted image, a proton density image map or other image. The image is based, at least in part, on the quantitative values retrieved at 1450. With additional information available concerning diffusion or perfusion, the image may also be based, at least in part, on the diffusion or perfusion information.

Figure 16:
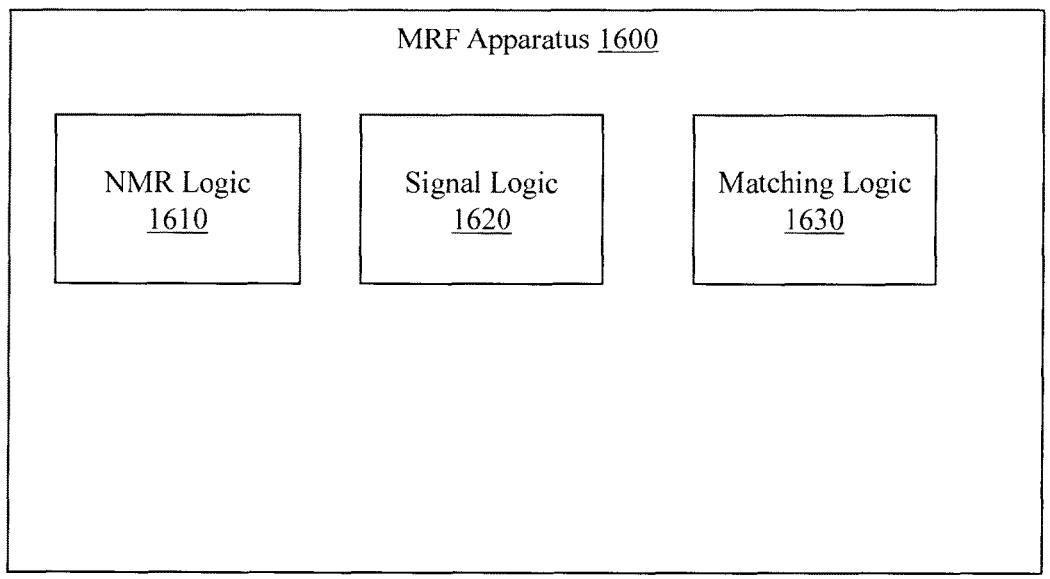
FIG. 16 illustrates an example MR apparatus associated with MRF-FISP.

FIG. 16 illustrates an MRF apparatus 1600. MRF apparatus 1600 simultaneously quantifies MR parameters including T1, T2, and proton density for an object to which an MRF-FISP pulse sequence is applied. MRF apparatus 1600 includes an NMR logic 1610. In one embodiment, the NMR logic 1610 applies RF energy to the object according to an MRF-FISP pulse sequence. The MRF-FISP sequence has at least one unbalanced gradient that dephases transverse magnetization produced by the MRF apparatus 1600.

NMR logic 1610 repetitively and variably samples an object in a (k, t, E) space to acquire a first set of data. The first set of data may be a set of NMR signals that may have non-constant amplitude and/or phase. Members of the set of NMR signals are associated with different points in the (k, t, E) space. In different embodiments the different points are sampled according to a plan where t and/or E varies non-linearly and/or in a non-constant manner.

In one embodiment, the first set of data is less sensitive to B0 inhomogeneity than data acquired in response to a pulse sequence that does not have an unbalanced gradient that dephases transverse magnetization. Additionally, the first set of data may be more sensitive to spin diffusion in the object than data acquired in response to a pulse sequence that does not have an unbalanced gradient that dephases transverse magnetization. Similarly, the first set of data may be more sensitive to perfusion in the object than data acquired in response to a pulse sequence that does not have an unbalanced gradient that dephases transverse magnetization.

In one embodiment, NMR logic 1610 may use a spiral readout to acquire the first set of data. The NMR logic 1610 may control the MRF-FISP pulse sequence to use a variable density spiral trajectory with minimum time gradient design. The NMR logic 1610 may control the variable density spiral trajectory to use first interleaves to fully sample an inner region of k-space associated with the object. Additionally, the NMR logic 1610 may control the variable spiral trajectory to use second different interleaves to fully sample an outer region of k-space associated with the object.

MRF apparatus 1600 also includes a signal logic 1620. Signal logic 1620 produces an NMR signal evolution from the acquired NMR signals. The signal evolution may include a number of NMR signals acquired over a period of time.

MRF apparatus 1600 also includes a matching logic 1630. Matching logic 1630 compares the produced NMR signal evolution or information associated with the produced NMR signal evolution to reference information and identifies a stored signal related to the NMR signal evolution. "Match" as used herein refers to the result of comparing signals. "Match" does not refer to an exact match, which may or may not be found. A match may be the signal that most closely resembles another signal. A match may be the first signal that matches another signal to within a threshold. A match may be found by template matching, pattern matching, or other comparison approaches. The reference information may be, for example, a previously acquired signal evolution, a simulated signal evolution, an item derived from a signal evolution other than the produced NMR signal evolution, and other information. The reference information may include signal evolutions from different tissue types (e.g., healthy, diseased, advanced disease).

In one embodiment, the collection of stored signal evolutions is produced using an extended phase graph approach. The collection of stored signal evolutions include a signal selected from:

$$SE = \sum_{i=1}^{N_S} \prod_{i=1}^{N_A} \sum_{j=1}^{N_{RF}} R_{i(\alpha)} R_{RF_{ij}(\alpha,\phi)} R(G) E_i(T1, T2, \ldots) DPdM_0$$

or $$SE = \sum_{i=1}^{N_S} \prod_{i=1}^{N_A} \prod_{j=1}^{N_{RF}} R_{i(\alpha)} R_{RF_{ij}(\alpha,\phi)} R(G) E_i(T1, T2, \ldots) DPdM_0$$

where:
SE is a signal evolution,
$N_S$ is a number of spins,
$N_A$ is a number of sequence blocks,
$N_{RF}$ is a number of RF pulses in a sequence block,
$\alpha$ is a flip angle,
$\Phi$ is a phase angle,
Ri($\alpha$) is a rotation due to off resonance,
$R_{RFij}(\alpha,\Phi)$ is a rotation due to RF differences,
R(G) is a rotation due to a gradient,
T1 is spin-lattice relaxation,
T2 is spin-spin relaxation,
D is diffusion relaxation,
Pd is proton density,
$E_i(T1, T2, \ldots)$ is decay due to relaxation differences, and
$M_0$ is the default or equilibrium magnetization.

In one embodiment, the collection of stored signal evolutions include a signal selected from:

$$S_i = R_i E_i (S_{i-1})$$

or $$S_i = R_i E_i \sum_{x=1}^{i-1} R_x E_x (S_x)$$

or $$S_i = R_i E_i \prod_{x=1}^{i-1} R_x E_x (S_x)$$

or $$S_i = \sum_{s=1}^{N_s} R_{s,i} E_{s,i} (S_{s,i-1})$$

or $$S_i = \sum_{s=1}^{N_s} R_{s,i} E_{s,i} \sum_{x=1}^{i-1} R_{s,x} E_{s,x} (S_{s,x})$$

or $$S_i = \sum_{s=1}^{N_S} R_{s,i} E_{s,i} \prod_{x=1}^{i-1} R_{s,x} E_{s,x}(S_{s,x})$$

where:

$S_O$ is the default or equilibrium magnetization.

$S_i$ is a vector that represents the different components of the magnetization Mx, My, Mz during acquisition block i, $R_i$ is the combination of rotational effects that occur during acquisition block i, and $E_i$ is the combination of effects that alter the amount of magnetization in the different states for acquisition block i.

Figure 17:
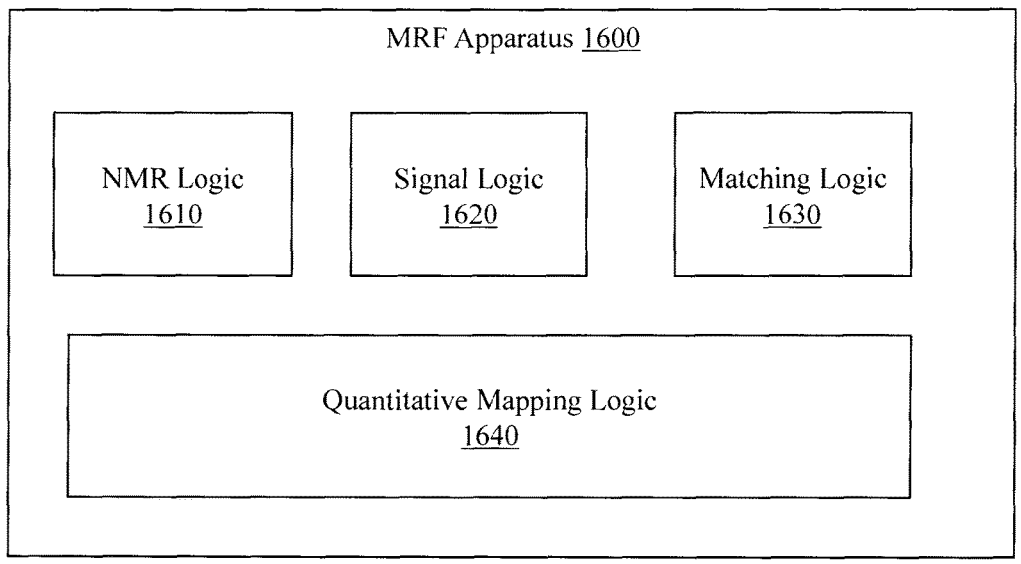
FIG. 17 illustrates an example MR apparatus associated with MRF-FISP.

FIG. 17 illustrates another embodiment of apparatus 1600. This embodiment also includes a quantitative mapping logic 1640. In one embodiment, the quantitative mapping logic 1640 simultaneously produces quantitative maps for T1, T2, or proton density associated with the object. The maps may be based, at least in part, on the stored signal evolution that matches the NMR signal evolution. In one embodiment, the quantitative mapping logic 1640 may display the quantitative maps. In one embodiment, the quantitative mapping logic 1640 may produce a magnetic resonance image that is based, at least in part, on the first set of data, the NMR signal evolution, and the stored signal related to the NMR signal evolution.

While matching logic 1630 and quantitative mapping logic 1640 are illustrated as being part of MRF apparatus 1600, in one embodiment, the matching logic 1630 and quantitative mapping logic 1640 may reside in an apparatus separate from the MRF apparatus 1600. In this embodiment, MRF apparatus 1600 may provide NMR signals to the separate apparatus housing matching logic 1630 or quantitative mapping logic 1640. In one embodiment, matching logic 1630 or quantitative mapping logic 1640 may reside in separate apparatus.

Figure 18:
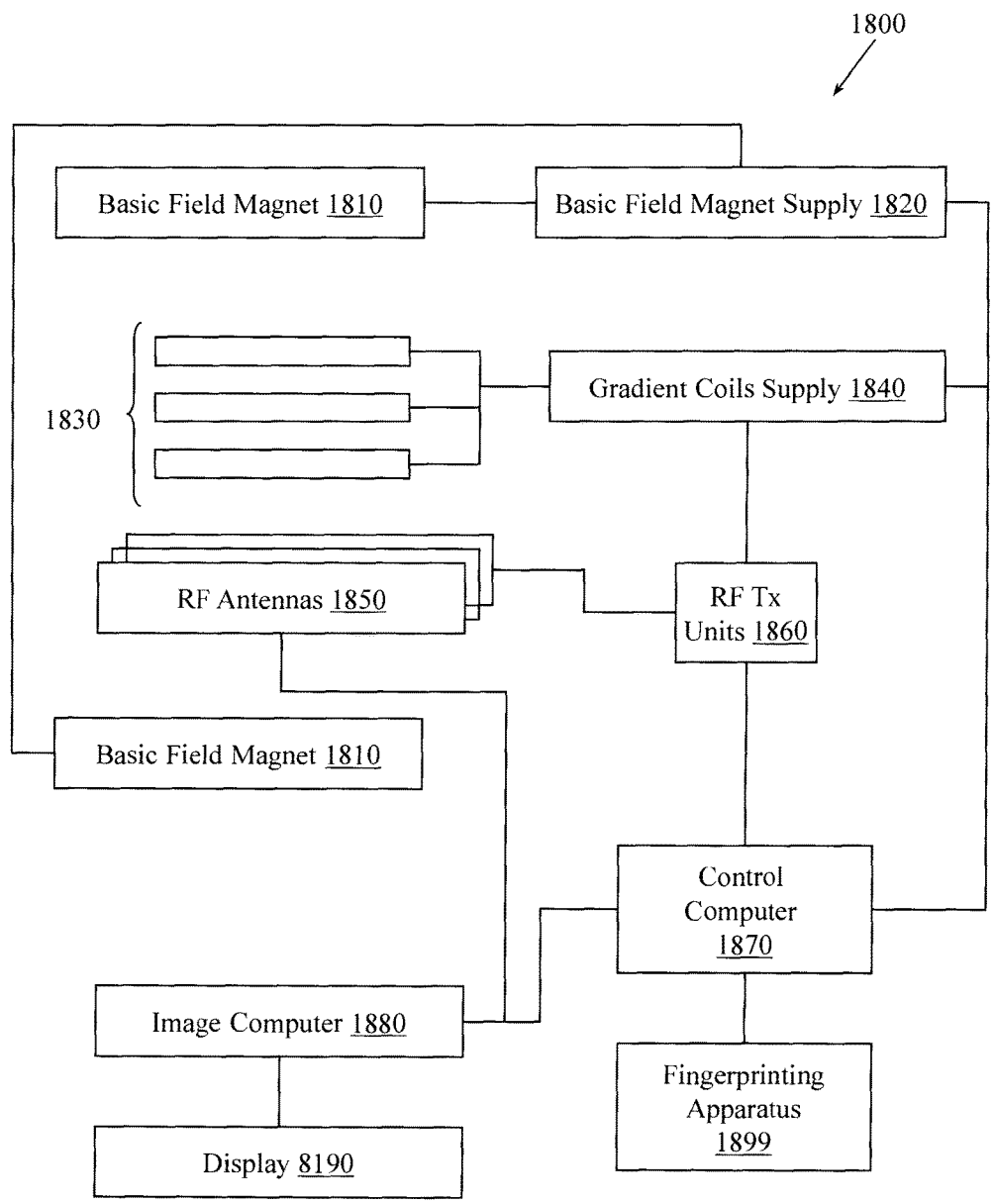
FIG. 18 illustrates an example MR apparatus associated with MRF-FISP.

FIG. 18 illustrates an example MR apparatus 1800 configured with a fingerprinting apparatus 1899 to facilitate MRF using an MRF-FISP pulse sequence that simultaneously quantifies T1, T2, proton density, or other MR parameters (e.g., diffusion, perfusion). The fingerprinting apparatus 1899 may be configured with elements of example apparatus described herein or may perform example methods described herein. While fingerprinting apparatus 1899 is illustrated as part of MR apparatus 1800, in one example, fingerprinting apparatus 1899 may be a separate apparatus or apparatuses.

The apparatus 1800 includes a basic field magnet(s) 1810 and a basic field magnet supply 1820. Ideally, the basic field magnets 1810 would produce a uniform B0 field. However, in practice, the B0 field may not be uniform, and may vary over an object being analyzed by the MR apparatus 1800. Using the MRF-FISP sequence with an unbalanced gradient as described herein may make data acquired from the object less sensitive to an inhomogeneous B0 field by controlling the dephasing of transverse magnetization. MR apparatus 1800 may include gradient coils 1830 that emit gradient magnetic fields like $G_S$, $G_P$ and $G_R$. The gradient coils 1830 may be controlled, at least in part, by a gradient coils supply 1840. In some examples, the timing, strength, and orientation of the gradient magnetic fields may be controlled, and thus selectively adapted, during an MR procedure.

MR apparatus 1800 may include a set of RF antennas 1850 that generate RF pulses and receive resulting NMR signals from an object to which the RF pulses are directed. In some examples, how the pulses are generated and how the resulting MR signals are received may be controlled and thus may be selectively adapted during an MR procedure. Separate RF transmission and reception coils can be employed. The RF antennas 1850 may be controlled, at least in part, by a set of RF transmission units 1860. An RF transmission unit 1860 may provide a signal to an RF antenna 1850.

The gradient coils supply 1840 and the RF transmission units 1860 may be controlled, at least in part, by a control computer 1870. In one example, the control computer 1870 may be programmed to control an NMR device as described herein. Conventionally, the MR signals received from the RF antennas 1850 can be employed to generate an image and thus may be subject to a transformation process like a two dimensional FFT that generates pixilated image data. The transformation can be performed by an image computer 1880 or other similar processing device. The image data may then be shown on a display 1890.

Fingerprinting apparatus 1899 facilitates not having to do conventional reconstruction of an image from MR signals received from the RF antennas 1850. Thus the RF energy applied to an object by apparatus 1800 need not be constrained to produce signals with substantially constant amplitudes or phases. Instead, fingerprinting apparatus 1899 facilitates matching received signals to known signals for which a reconstruction, relaxation parameter, or other information is already available.

In one embodiment, fingerprinting apparatus 1899 may include a data store that stores a dictionary of MRF signal evolutions. Fingerprinting apparatus 1899 may also include a collection logic that collects a received signal evolution from a tissue experiencing NMR in response to an MRF excitation applied to the tissue by apparatus 1800. The MRF excitation is applied according to an MRF-FISP pulse sequence having an unbalanced gradient that dephases transverse magnetization produced in the tissue by the apparatus 1800. The fingerprinting apparatus 1899 may also include a selection logic that selects a member of the dictionary that is most closely related to the signal evolution. Once the member of the dictionary that is most closely related to the signal evolution has been selected, a characterization logic in fingerprinting apparatus 1899 may identify a T1 relaxation value, a T2 relaxation value, a proton density value, or other MR parameter values for the tissue. Since the signal acquired from the tissue is less sensitive to B0 fluctuations, the characterization logic may also identify a diffusion value for the tissue or a perfusion value for the tissue. The fingerprinting apparatus 1899 may also include an image logic that produces a magnetic resonance image from a plurality of signal evolutions received from the tissue. The magnetic resonance image is based, at least in part, on a plurality of values produced by the characterization logic for T1 relaxation, T2 relaxation, proton density, or other MR parameter values.

While FIG. 18 illustrates an example MR apparatus 1800 that includes various components connected in various ways, it is to be appreciated that other MR apparatus may include other components connected in other ways.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is inclusive in a manner similar to the term "comprising" as that term is interpreted when employed as a transitional word in a claim.

To the extent that the term "or" is employed in the detailed description or claims (e.g., A or B) it means "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. A method for controlling a magnetic resonance fingerprinting apparatus, the method comprising:
   accessing a set of known signal evolutions;
   accessing an acquired nuclear magnetic resonance (NMR) signal, where the acquired NMR signal was produced by a volume that contains one or more resonant species that simultaneously produced individual NMR signals in response to magnetic resonance fingerprinting (MRF) excitation that employed a steady state free precession (MRF-FISP) pulse sequence;
   controlling the MRF-FISP pulse sequence to employ a variable density spiral readout trajectory;
   determining a signal evolution from the acquired NMR signal;
   finding a selected entry in the set of known signal evolutions that matches the signal evolution; and
   retrieving, from stored magnetic resonance (MR) parameters associated with the selected entry, quantitative values for T1 relaxation associated with the resonant species, T2 relaxation associated with the resonant species, or a proton density associated with the resonant species, T1 being spin-lattice relaxation, T2 being spin-spin relaxation.

2. The method of claim 1, comprising:
   simultaneously producing, from the quantitative values, quantitative maps associated with the T1 relaxation, the T2 relaxation, and the proton density.

3. The method of claim 1, comprising:
   retrieving, from stored MR parameters associated with the selected entry, quantitative values for a diffusion parameter associated with the resonant species or a perfusion parameter associated with the resonant species.

4. The method of claim 3, comprising producing an image based, at least in part, on the quantitative values for the diffusion parameter or the perfusion parameter.

5. The method of claim 1, comprising controlling the variable density spiral readout trajectory to use M interleaves to fully sample an inner region of k space, M being an integer, and to use N interleaves to fully sample an outer region of k space, N being an integer greater than M.

6. The method of claim 1, comprising controlling the variable density spiral readout trajectory to use one spiral interleaf per acquisition period.

7. The method of claim 1, comprising controlling the variable density spiral readout trajectory to rotate per acquisition period.

8. The method of claim 1, comprising varying acquisition times in the MRF-FISP pulse sequence from acquisition period to acquisition period.

9. The method of claim 1, where the set of known signal evolutions includes signal evolutions outside the set of signal evolutions characterized by:

$$SE = A - Be^{-t/C}$$

where:
SE is a signal evolution,
A is a constant,
B is a constant,
t is time, and
C is a single relaxation parameter.

10. The method of claim 1, where the set of known signal evolutions includes a signal selected from a set of signals described by:

$$SE = \sum_{i=1}^{N_S} \prod_{i=1}^{N_A} \sum_{j=1}^{N_{RF}} R_{i(\alpha)} R_{RF_{ij}(\alpha,\phi)} R(G) E_i(T1, T2, K) DPdM_0$$

or $$SE = \sum_{i=1}^{N_S} \prod_{i=1}^{N_A} \prod_{j=1}^{N_{RF}} R_{i(\alpha)} R_{RF_{ij}(\alpha,\phi)} R(G) E_i(T1, T2, K) DPdM_0$$

where:
SE is a signal evolution,
$N_S$ is a number of spins,
$N_A$ is a number of sequence blocks,
$N_{RF}$ is a number of RF pulses in a sequence block,
α is a flip angle,
Φ is a phase angle,
Ri(α) is a rotation due to off resonance,
$R_{RFij}(\alpha, \Phi)$ is a rotation due to RF differences,
R(G) is a rotation due to a gradient,
T1 is spin-lattice relaxation,
T2 is spin-spin relaxation,
D is diffusion relaxation,
Pd is proton density,
$E_i(T1,T2, \ldots)$ is decay due to relaxation differences, and
$M_0$ is the default or equilibrium magnetization.

11. The method of claim 1, where the set of known signal evolutions includes a signal selected from a set of signals described by:

$$S_i = R_i E_i \sum_{x=1}^{i-1} R_x E_x(S_x)$$

or $$S_i = R_i E_i \prod_{x=1}^{i-1} R_x E_x(S_x)$$

where:
$S_0$ is the default or equilibrium magnetization,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

12. The method of claim 1, where the set of known signal evolutions includes a signal selected from a set of signals described by:

$$S_i = \sum_{s=1}^{N_s} R_{s,i} E_{s,i}(S_{s,i-1})$$

where:
$S_0$ is the default or equilibrium magnetization,
Ns is the number of spins,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

13. The method of claim 1, where the set of known signal evolutions includes a signal selected from a set of signals described by:

$$S_i = \sum_{s=1}^{N_s} R_{s,i} E_{s,i} \sum_{x=1}^{i-1} R_{s,x} E_{s,x}(S_{s,x})$$

or $$S_i = \sum_{s=1}^{N_s} R_{s,i} E_{s,i} \prod_{x=1}^{i-1} R_{s,x} E_{s,x}(S_{s,x})$$

where:
$S_0$ is the default or equilibrium magnetization,
$N_s$ is the number of spins,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i.

14. The method of claim 1, comprising producing an image based, at least in part, on the quantitative values for the T1 relaxation, the T2 relaxation, or the proton density.

15. The method of claim 1, where the MRF-FISP pulse sequence includes an inversion recovery period.

16. A method for controlling a magnetic resonance fingerprinting apparatus, the method comprising:
accessing a set of known signal evolutions;
accessing an acquired nuclear magnetic resonance (NMR) signal, where the acquired NMR signal was produced by a volume that contains one or more resonant species that simultaneously produced individual NMR signals in response to magnetic resonance fingerprinting (MRF) excitation that employed a steady state free precession (MRF-FISP) pulse sequence;
controlling the MRF-FISP pulse sequence to have an unbalanced gradient in between applications of RF pulses that dephases transverse magnetization produced in the volume;
determining a signal evolution from the acquired NMR signal;
finding a selected entry in the set of known signal evolutions that matches the signal evolution; and
retrieving, from the stored magnetic resonance (MR) parameters associated with the selected entry, quantitative values or T1 relaxation associated with the resonant species, T2 relaxation associated with the resonant species, or a proton density associated with the resonant species, T1 being spin-lattice relaxation, T2 being spin-spin relaxation.

17. The method of claim 16, where the unbalanced gradient dephases transverse magnetization up to $2\pi$ within one voxel.

18. The method of claim 16, where the unbalanced gradient dephases transverse magnetization more than $2\pi$ within one voxel.

19. The method of claim 16, where the acquired NMR signal is insensitive to B0 inhomogeneity due, at least in part, to the unbalanced gradient that dephases the transverse magnetization.

20. A method for controlling a magnetic resonance fingerprinting apparatus, the method comprising:
determining a set of known signal evolutions using an extended phase graph approach;
accessing a set of known signal evolutions;
accessing an acquired nuclear magnetic resonance (NMR) signal, where the acquired NMR signal was produced by a volume that contains one or more resonant species that simultaneously produced individual NMR signals in response to magnetic resonance fingerprinting (MRF) excitation that employed a steady state free precession (MRF-FISP) pulse sequence;
determining a signal evolution from the acquired NMR signal;
finding a selected entry in the set of known signal evolutions that matches the signal evolution; and
retrieving, from the stored magnetic resonance (MR) parameters associated with the selected entry, quantitative values or T1 relaxation associated with the resonant species, T2 relaxation associated with the resonant species, or a proton density associated with the resonant species, T1 being spin-lattice relaxation, T2 being spin-spin relaxation.

21. A method for controlling a magnetic resonance fingerprinting apparatus, the method comprising:
accessing a set of known signal evolutions;
accessing an acquired nuclear magnetic resonance (NMR) signal, where the acquired NMR signal was produced by a volume that contains one or more resonant species that simultaneously produced individual NMR signals in response to magnetic resonance fingerprinting (MRF) excitation that employed a steady state free precession (MRF-FISP) pulse sequence;
varying flip angles in the MRF-FISP pulse sequence from acquisition period to acquisition period;
determining a signal evolution from the acquired NMR signal;
finding a selected entry in the set of known signal evolutions that matches the signal evolution; and
retrieving, from the stored magnetic resonance (MR) parameters associated with the selected entry, quantitative values or T1 relaxation associated with the resonant species, T2 relaxation associated with the resonant species, or a proton density associated with the resonant species, T1 being spin-lattice relaxation, T2 being spin-spin relaxation.

22. The method of claim 21, comprising varying acquisition times in the MRF-FISP pulse sequence from acquisition period to acquisition period.

23. A method for controlling a magnetic resonance fingerprinting apparatus, the method comprising:
accessing a set of known signal evolutions;
accessing an acquired nuclear magnetic resonance (NMR) signal, where the acquired NMR signal was produced by a volume that contains one or more resonant species that simultaneously produced individual NMR signals in response to magnetic resonance fingerprinting (MRF) excitation that employed a steady state free precession (MRF-FISP) pulse sequence;
controlling the MRF apparatus to produce the MRF excitation using the MRF-FISP pulse sequence by applying radio frequency (RF) energy to the volume in an object in a series of variable sequence blocks, where a sequence block includes one or more excitation phases, one or more readout phases, and one or more waiting phases,
where the MRF-FISP pulse sequence has an unbalanced gradient between RF pulses that dephases transverse magnetization produced in the volume,
where the RF energy applied during a sequence block causes the one or more resonant species in the volume to simultaneously produce individual NMR signals, and
where at least one member of the series of variable sequence blocks differs from at least one other member of the series of variable sequence,
controlling the MRF apparatus to acquire the simultaneously produced individual NMR signals,
determining a signal evolution from the acquired NMR signal;
finding a selected entry in the set of known signal evolutions that matches the signal evolution; and
retrieving, from the stored magnetic resonance (MR) parameters associated with the selected entry, quantitative values or T1 relaxation associated with the resonant species, T2 relaxation associated with the resonant species, or a proton density associated with the resonant species, T1 being spin-lattice relaxation, T2 being spin-spin relaxation.

24. The method of claim 23, where the sequence block parameters include echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, an amount by which a gradient is unbalanced when applied between an excitation portion of a sequence block and a readout portion of a sequence bock, a type of gradient applied between a readout portion of a sequence block and an excitation portion of a sequence block, a number of gradients applied between a readout portion of a sequence block and an excitation portion of a sequence block, an amount by which a gradient is unbalanced when applied between a readout portion of a sequence block and an excitation portion of a sequence bock, a type of gradient applied during a readout portion of a sequence block, a number of gradients applied during a readout portion of a sequence block, an amount of RF spoiling, or an amount of gradient spoiling.

25. The method of claim 24, comprising:
controlling the MRF apparatus to vary an amount of time between sequence blocks in the series of variable sequence blocks, the relative amplitude of RF pulses in sequence blocks in the series of variable sequence blocks, or the relative phase of RF pulses in sequence blocks in the series of variable sequence blocks.

26. A method for controlling a magnetic resonance fingerprinting apparatus, the method comprising:
accessing a set of known signal evolutions;
where the set of known signal evolutions includes a signal selected from a set of signals described by:

$$S_i = R_i E_i (S_{i-1})$$

where:
$S_0$ is the default or equilibrium magnetization,
$S_i$ is a vector that represents the different components of the magnetization Mx, My, Mz during acquisition block i,
$R_i$ is the combination of rotational effects that occur during acquisition block i, and
$E_i$ is the combination of effects that alter the amount of magnetization in the different states for acquisition block i;
accessing an acquired nuclear magnetic resonance (NMR) signal, where the acquired NMR signal was produced by a volume that contains one or more resonant species that simultaneously produced individual NMR signals in response to magnetic resonance fingerprinting (MRF) excitation that employed a steady state free precession (MRF-FISP) pulse sequence;
determining a signal evolution from the acquired NMR signal;
finding a selected entry in the set of known signal evolutions that matches the signal evolution; and
retrieving, from the stored magnetic resonance (MR) parameters associated with the selected entry, quantitative values or T1 relaxation associated with the resonant species, T2 relaxation associated with the resonant species, or a proton density associated with the resonant species, T1 being spin-lattice relaxation, T2 being spin-spin relaxation.

* * * * *